United States Patent [19]
Klement

[11] Patent Number: 5,201,755
[45] Date of Patent: Apr. 13, 1993

[54] METHOD AND APPARATUS FOR EARLY DETECTION OF LEAKAGE AND FAILURE OF A BALLOON MEMBRANE OF A BALLOON CATHETER

[75] Inventor: Haim Klement, Montvale, N.J.

[73] Assignee: Datascope Investment Corp., Montvale, N.J.

[21] Appl. No.: 580,472

[22] Filed: Sep. 11, 1990

[51] Int. Cl.$^5$ .................... A61B 17/00; A61B 5/027
[52] U.S. Cl. ................................ 606/194; 128/713
[58] Field of Search ............... 128/634, 665, 713; 606/194, 195

[56] References Cited

U.S. PATENT DOCUMENTS

| | | | |
|---|---|---|---|
| 4,200,110 | 4/1980 | Peterson et al. | 128/634 |
| 4,522,194 | 6/1985 | Normann | 600/18 |
| 4,854,321 | 8/1989 | Boiarski | 128/634 |
| 4,889,407 | 12/1989 | Markle et al. | 350/96.29 |
| 5,019,075 | 5/1991 | Spears et al. | 606/7 |
| 5,020,537 | 6/1991 | Günther | 128/634 |

Primary Examiner—Lee S. Cohen
Assistant Examiner—Kevin Pontius
Attorney, Agent, or Firm—Fitzpatrick, Cella, Harper & Scinto

[57] ABSTRACT

A method and system for detecting damage to a balloon catheter and presence of a contaminant within the balloon catheter by irradiating a reflector located toward the distal end of the catheter tube and measuring reflectivity. By detecting a change in the reflected radiation, it is possible to identify the presence of a contaminant and the occurrence of leakage. The method and system of the present invention also permits the operator to determine deterioration of the parts of the system that detect the presence of a contaminant.

43 Claims, 4 Drawing Sheets

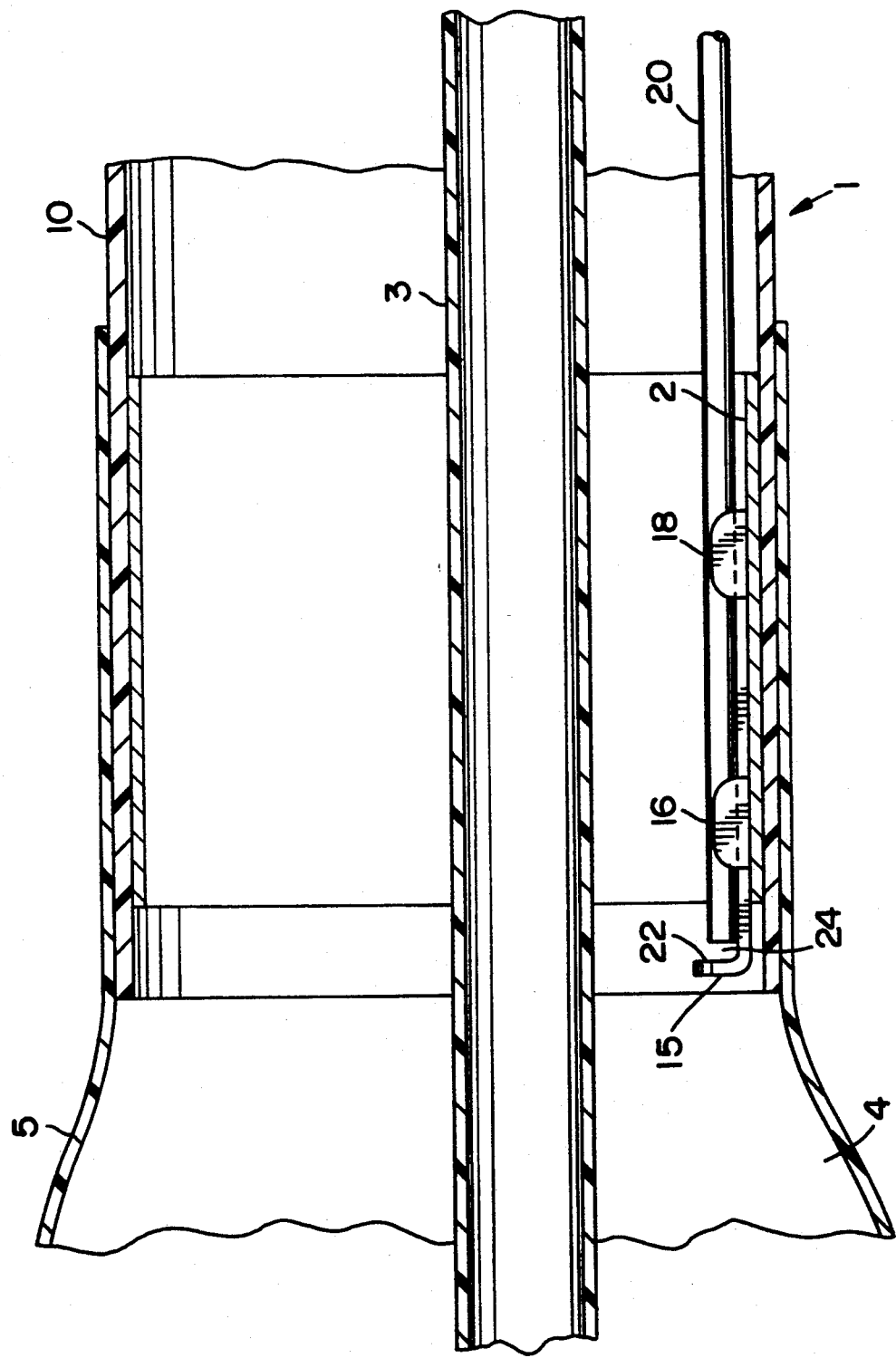

METHOD AND APPARATUS FOR EARLY DETECTION OF LEAKAGE AND FAILURE OF A BALLOON MEMBRANE OF A BALLOON CATHETER

BACKGROUND OF THE INVENTION

1. Field of the Invention

The present invention relates generally to balloon catheters of the type that are inserted into the vascular system. More particularly, the invention relates to a system and method for detecting the presence of minute quantities of a contaminant, such as blood, within the balloon chamber of a balloon catheter. The invention is believed to offer three particularly useful advantages: (1) it permits sensitive and early detection of failure of membrane integrity should the membrane be damaged, as during an intra-aortic procedure using a balloon catheter, (2) it provides a method for determining significant deterioration of the system, and (3) it permits detection of leakage of a contaminant such as blood into the balloon chamber much more rapidly than was previously possible by traditional methods.

2. Related Background

Balloon catheters having use in medical procedures requiring introduction into the vascular system are well known. Such catheters typically have a catheter portion with proximal and distal ends, and a balloon portion located at or near the distal end of the catheter portion.

The balloon catheter for which the subject invention is believed to be most useful is the intra-aortic balloon catheter. The invention herein disclosed, however, is not limited to use in such devices.

Conventional intra-aortic balloon catheters have non-distensible balloons that conventionally are inflated with either helium or carbon dioxide provided through the catheter portion by an external pump console connected at the proximal end of the catheter. The catheter portions are preferably quite flexible as well as soft, in order to facilitate their negotiation through the vascular system. The entire balloon catheter may have a length of up to two and a half to three feet, with the balloon portion comprising up to ten inches. Typically, the balloon chamber, when inflated, has a volume of about 40 cc, although larger and smaller balloons are not uncommon.

It is well known that atherosclerotic plaques, for example, can be quite hard and may have sharp edges. Consequently, the possibility exists that balloons or other portions of balloon catheters may be damaged or punctured by the plaques or other deposits within the vascular system. Such damage could cause leakage of the inflating gas into the patient's vascular system, as well as leakage of blood into the balloon chamber. Therefore, prompt detection of any damage to the balloon is of the utmost importance.

Detection of such damage has previously been very difficult. For example, intra-aortic balloon catheters typically contain gas in a closed system. A fixed volume of gas is pumped or shuttled back and forth between the balloon resident in the patient's aorta and the balloon in the pump console. If the integrity of the balloon within the body of the patient is compromised, gas will leak from the closed system into the blood vessel of the patient and the reduction in gas volume will trigger an alarm, alerting the operator. However, the volumetric triggers of such closed system catheters have certain limitations. Typically, they cannot be made adequately sensitive without risking frequent false alarms. Consequently, these volumetric triggers generally do not respond until a significant amount of gas has escaped from the closed system.

The instant invention overcomes the drawbacks of volumetric sensors by using a light reflector/detector system. Light is transmitted through an optical fiber to the balloon chamber where it is reflected back to a sensor. Any change in reflected light, whether it be in intensity, color or the like, can then be detected and used to trigger the alarm.

It has been found that when the balloon membrane has been damaged, not only does inflating gas tend to escape, but, in addition, blood also tends to enter the balloon chamber. The instant invention, instead of reacting to a reduced gas volume, reacts to the presence of blood, or some other contaminant, in the chamber. Since the presence of even the smallest amount of blood inside the balloon is cause for concern, the detection system of the instant invention can be made far more sensitive, and with greater rapidity of response, than volumetric detectors.

In other arts, fiber optical probes have been used to determine, for example, pH and properties of chemical in living tissue. To illustrate, Costello U.S. Pat. No. 4,682,895 relates to a fiber optic probe that includes two optical fibers enclosed in a semipermeable membrane. A colorimetric substance is contained in a sample chamber. A sample chemical permeates the membrane and the colorimetric substance. If the property to be tested is present in the chemical, the colorimetric substance will change color and its transmissivity will be altered, signalling the presence of the property to be detected. According to Costello, light transmitted along the optical fiber traverses the sample chamber and is detected by another optical fiber that is disposed opposite to the transmitting fiber. Such a system, however, only considers the specific chemical property to be tested, and cannot detect the presence of contaminants.

Peterson, et al. U.S. Pat. No. 4,200,110 relates to a fiber optic probe for determining the pH of living tissue. A pH sensitive dye is provided within an ion permeable membrane that encloses the ends of two optical fibers. Peterson's probe determines pH based on a change in color of the pH sensitive dye. This probe, however, cannot detect the presence of contaminants.

Wicnienski U.S. Pat. No. 4,350,441 relates to a photometric system for determining an absorbance ratio of two different wavelengths of light passed alternately through a sample. A similar system is described in Bilstad, et al. U.S. Pat. No. 4,305,659.

According to Bilstad, et al., a first light is given a reference intensity, and a second light is varied so that its intensity matches that of the first light after it passes through a sample. Absorbance is calculated based on a ratio of the absorbance of the second light where its intensity is equal to a state in which it has not passed through a sample, and the absorbance of the first light. Neither system is designed to determine the presence of contaminants in a catheter, nor do they solve the above-described problems of traditional methods for detecting catheter failure.

SUMMARY OF THE INVENTION

It is therefore an object of the present invention to provide a sensitive method for detecting the leakage of a contaminant, such as blood, into a chamber, such as the balloon of a balloon catheter.

It is further an object of the present invention to provide a method for detecting the leakage of a contaminant such as blood into a chamber, such as the balloon of a balloon catheter, far more rapidly than is possible with traditional methods.

Another object of the invention is to provide a method for assessing deterioration of the leakage sensor.

A further object of the invention is to provide a system for performing the method of the invention.

According to the broad concept of the present invention, these objects are achieved by transmitting electromagnetic radiation to the region where the contaminant is to be detected, reflecting that radiation to a sensor, and providing means for detecting the changes that the presence of a contaminant will cause in that reflected radiation.

In the preferred embodiment, electromagnetic radiation is provided in the form of light transmitted through an optical fiber placed within the lumen of the catheter and into the balloon. A mirrored surface is mounted onto the end of the fiber, leaving a narrow gap therebetween. The gap is made sufficiently small so that capillary action will draw blood into it.

Light transmitted by the optical fiber traverses the contaminant-filled narrow gap and is reflected back into the fiber by the mirrored surface. Because the contaminant partially absorbs the light from the optical fiber, it is possible to determine whether a contaminant is present by measuring the intensity of the reflected light. By this method, the presence of even small quantities of contaminant, indicating only minor damage to the membrane, may be rapidly detected with greater sensitivity than is possible with traditional methods.

In another embodiment, the presence of a contaminant is detected by measuring the change in physical property, such as color, of an absorbent medium placed within the balloon of a balloon catheter. In its original state, the absorbent medium may be white. The absorbent medium is chosen so that its color changes when it absorbs a contaminant, such as blood, that may leak into the balloon chamber. This change in color is determined by illuminating the absorbent medium with light, and detecting the reflected light. By determining the intensity or wavelength of the reflected light, it is possible to identify whether the color of the absorbent medium has changed.

It should be understood that the present invention is not limited to the particular embodiments described herein. Other means for practicing the invention will readily occur to those skilled in the art. For example, damage to a balloon chamber can be detected by reflecting radiation off of the interior surface of the balloon membrane. Such reflectivity can be improved by coating the inside of the membrane with a reflective coating, for example, or other reflective and/or absorbent substance. These variations, as well as numerous others will be well understood by those skilled in the art to be possible without departing from the inventive concept.

In normal usage, a balloon catheter is placed within a fluid passageway, frequently an artery, of a patient's body. Since the balloon membrane is the most fragile element of the balloon catheter, that is the element that is most likely to be damaged. Accordingly, the present invention is directed to sense the presence of a contaminant in the balloon chamber. To that end, a reflector is preferably placed within the catheter tube immediately adjacent the balloon junction. However, damage to the catheter portion may also be detected if the reflector is positioned within the balloon chamber itself. Also disposed within the balloon catheter is apparatus for irradiating the reflector with light, and apparatus for detecting light reflected therefrom. Although one wavelength of light or a single beam of white light may be used, it is preferable that monitoring be accomplished by irradiating the reflector with at least two beams of light having different wavelengths. The different beams may take different light paths or they may sequentially follow the same path. The light reflected from the reflector is detected, measured, and compared to determine any change in physical property such as color, or reduction in intensity.

The present invention is both sensitive in its ability to detect minute quantities of blood, such as approximately 0.5 cc, and its rapid responsiveness to damage to the balloon.

The sensitivity of the present invention has the further advantage of providing a ready means of detecting significant deterioration of the sensor within the balloon catheter. For example, if the mirrored surface of the preferred embodiment becomes discolored or clouded, or if the optical fiber fails to properly transmit or detect light, or if the narrow gap becomes blocked, the present invention alerts the operator that the sensor within the catheter lumen is not functioning properly and will not be able to detect damage to the catheter. Similarly, if the absorbent medium discolors, as in the second embodiment, the operator will be alerted.

Another feature of the instant invention is that it can be made insensitive to the presence of harmless contaminants. For example, it has been found that water vapor often passes through the catheter membrane. Therefore, the presence of water vapor does not indicate membrane damage. Since water is clear, a system employing the present invention can be made to "ignore", i.e., not react to the presence of such a contaminant.

As noted above, it is believed most advantageous to use light beams of two different wavelengths. Those wavelengths can be chosen so that a system according to the present invention can selectively react to some contaminants and not to others. The same can be accomplished by judicious selection of the absorbent medium. Such a medium can be chosen so as to change color in the presence of some contaminants but not others.

These and other objects, features and advantages of the present invention will become more fully apparent from the following detailed description of the preferred embodiments of this invention, taken in conjunction with the accompanying drawings. Further, although the description herein is made primarily in the context of an intra-aortic procedure because that is where it is believed the invention will have the most immediate and widespread applicability, it should be understood that the invention itself is not so limited. The invention may have application to any procedure where damage to a chamber resulting in leakage of contaminants is to be determined.

BRIEF DESCRIPTION OF THE DRAWINGS

FIG. 6 is a side view of the reflector end of an apparatus according to the subject invention, mounted in a dual lumen catheter.

DETAILED DESCRIPTION OF THE PREFERRED EMBODIMENTS

Figure 1:
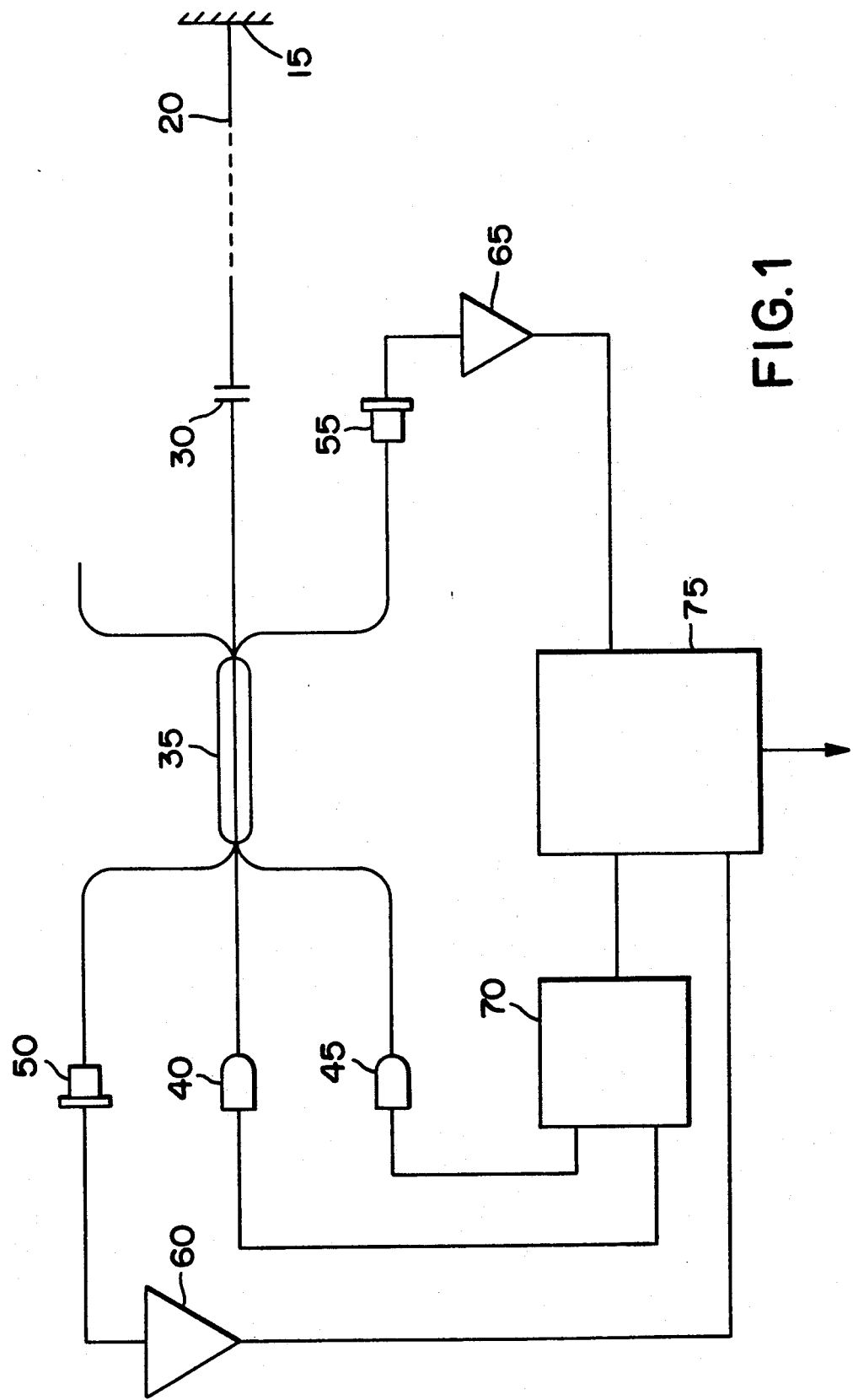
FIG. 1 is a schematic system diagram, according to the instant invention, for detecting leakage and deterioration of a balloon catheter.

The system employing the detection method of the subject invention includes a balloon catheter 1 having a balloon membrane 5 attached to a catheter tube 10. When inflated, balloon membrane 5 defines balloon chamber 4. Balloon catheter 1 may be a single lumen device or, as shown in FIG. 6, it may have a second or inner lumen 3 which extends through balloon chamber 4 to the distal tip of membrane 5. Catheter 1 may also be provided with a radiopaque marker 2.

An optical fiber 20 is run through the lumen of catheter tube 10 almost to the distal end of that tube. Opposite the end of fiber 20 is reflector 15. In the preferred embodiment, fiber 20 is securely fastened to bracket 14 by means of tabs 16 and 18. Bracket 14, in turn is securely fastened to radioopaque marker 2 which is itself securely fastened to the inner wall of catheter tube 10. Reflector 15, it should be noted, is part of bracket 14 so that when tabs 16 and 18 hold fiber 20 securely in the bracket, they also locate the face of fiber 20 relative to reflector 15. Reflector 15 is provided with mirrored face 22 which is positioned so that light emerging from the end of fiber 20 is reflected off mirror 22 back into fiber 20. The radioopaque marker, when present, provides a convenient anchor point but it is not a necessary element of the instant invention.

In the preferred embodiment, the end of fiber 20 and the reflector 15 are both situated inside the mouth of the catheter tube. However, they could also be located in balloon chamber 4. Optical fiber 20 preferably has a diameter of 250 microns, although other diameters may be chosen so that the optical fiber 20 and reflector 15 interfere as little as possible with the gas flow within the catheter.

As is best seen in FIGS. 3, 4, 5 and 6, a gap 24 is left between the distal end of fiber 20 and reflector 15. This narrow gap can have a width of 5 mils. Preferably the size of gap 24 is small enough so that capillary action will draw any contaminant into it. Other widths can be chosen, of course, but it is believed advantageous, although not absolutely necessary, that gap 24 be small enough to act as a capillary to liquids that may be present in the balloon chamber.

Figure 7:
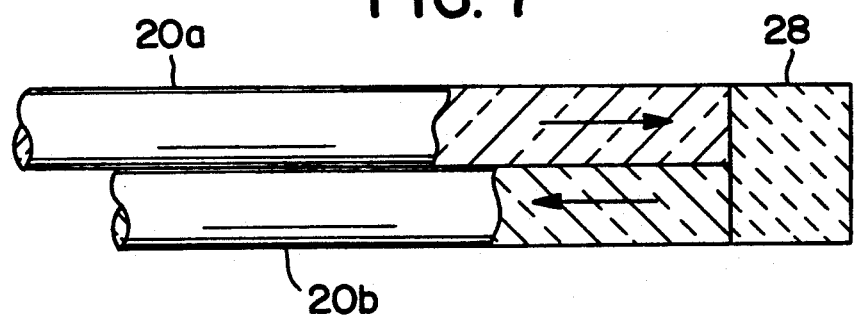
FIG. 7 is a side elevational view of the reflector end of an alternative embodiment of an apparatus, according to the instant invention.

FIG. 7 shows another embodiment wherein reflector 28 is in the form of an absorbent medium. Such a medium can be, for example, a solid piece of porous ceramic. Alternatively, it may consist of a powder within a sieve-like enclosure. In the context of the instant invention, the term "absorbent" means anything that changes color in the presence of a particular contaminant.

In the embodiment of FIG. 7, while believed to be preferable, it is not necessary for the absorbent medium to be in physical contact with optical fiber 20. All that is required is that light from the reflector be reflected to the fiber.

It should be noted that, the nature and structure of the reflector is not critical. In fact, it need not even be an additional element. For example, the inner surface of membrane 5 could serve as the reflector. In that case, its efficiency might be enhanced by use of a reflective coating.

The optical fiber may comprise a single fiber, as shown for example in FIGS. 3, 4, 5 and 6, or a plurality of fibers, as shown in FIG. 7. Moreover, while optical fibers are depicted in the drawings, any appropriate medium that will transmit electromagnetic radiation can be used. It is a purpose of the transmitting medium, preferably an optical fiber, to provide the path for both the transmitted as well as for the reflected radiation.

Optical fiber 20 is connected by an SMA connector 30 to a 3×3 fiber optic coupler 35. Coupler 35 is connected at its other end to light sources 40 and 45. In the preferred embodiment, light source 40 is a light emitting diode (LED) providing green light at a wavelength of 565 nm, and light source 45 is a light emitting diode (LED) providing red light at a wavelength of 635 nm. Other wavelengths may be selected in order to optimize the sensitivity and/or selectivity of the device to particular contaminants such as blood, for example.

Coupler 35 further connects optical fiber 20, by way of SMA connector 30, to sensor means comprised of PIN diode detector 50 and microcontroller 75. PIN detector 50 measures the reflected light from reflector 15 and conditioning amplifier 60 transmits the signals from PIN diode detector 50 to microcontroller 75, which has both analog to digital and digital to analog capability as is well known and understood in the art.

Coupler 35 also connects PIN diode detector 55 to the outputs of light sources 40 and 45. The signal transmitted through Coupler 35 from light sources 40 and 45 to SMA connector 30 and PIN diode detector 55, is in turn transmitted through conditioning amplifier 65 to microcontroller 75. Depending on the signal strength of the signals received by microcontroller 75, the light intensities may be varied by controller 70, which has LED drivers with amplitude control.

According to the operation of the preferred embodiment of the system and method of the invention, a balloon catheter is placed within a passageway of the body of a patient according to well known techniques. Monitoring for leakage of the balloon portion can be continued according to the invention throughout the period in which the balloon catheter is in place.

The light sources are operated in a three phase sequence: (1) off; (2) "green" on; and (3) "red" on. (The sequence can also be: (1) off; (2) "red" on; and (3) "green" on.) The strength of signals measured at the outputs of conditioning amplifier 60 and conditioning amplifier 65 are as follows:

Output of Amplifier 60

$S_d$—dark current (and offset) signal
$S_g$—"green" signal
$S_r$—"red" signal

Output of Amplifier 65

$R_d$—dark current (and offset) level reference
$R_g$—"green" level reference

Rr—"red" level reference

The system is initialized when new reflector means are connected to it. Green LEDs tend to be less efficient than red LEDs, such that the green light source 40 will therefore almost always operate at maximum rated current. Upon initialization, controller 70 adjusts the red light source 45 level so that the red signal strength equals the green signal strength according to the formula:

$Sgi = Sri$ (where i denotes initialization levels).

After adjustment, a reference ratio constant Kr is computed according to the formula:

$$Kr = (Rgi - Rdi)/(Rri - Rdi).$$

During monitoring, controller 70, which includes a low speed servo processor, varies the intensity of the red light source 45 to maintain the reference ratio (Kr) constant.

At intermittent periods during monitoring, microcontroller 75 of the sensor means determines the following ratio:

$$C = (Sg - Sd)/(Sr - Sd).$$

In the preferred embodiment, light passes through narrow gap 24 without interruption, and is reflected back to optical fiber 20 by mirrored surface 22. As long as no contaminant has been absorbed into narrow gap 24, the value of "C" is close to "1". However, if a contaminant such as blood is absorbed into gap 24, the value of "C" changes, and microcontroller 75 of the sensor means signals control and alarm messages. Alarm and caution thresholds may be determined without undue effort.

As an alternative, in the FIG. 7 embodiment, the absorbent medium of reflector 28 is white. As long as the absorbent medium remains white, the value of "C" remains close to 1. If reflector 28 changes color, for example due to the presence of blood, the value of "C" will change. As in the preferred embodiment, microcontroller 75 signals control and alarm messages when "C" changes. Determining alarm and caution thresholds for this embodiment may also be determined without undue effort.

Figure 2A:
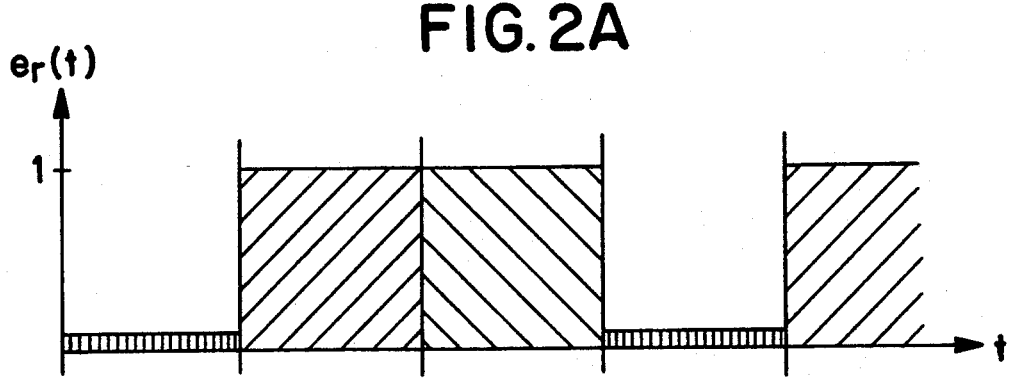
FIGS. 2A, 2B and 2C are graphic representations of the reflectance signals for a "white" target (FIG. 2A), a "red" target (FIG. 2B), and a "green" target (FIG. 2C).
Figure 2B:
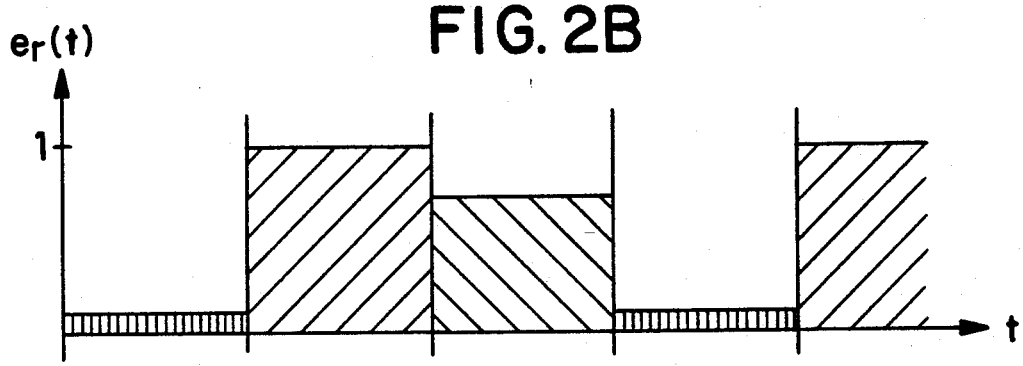
Figure 2C:
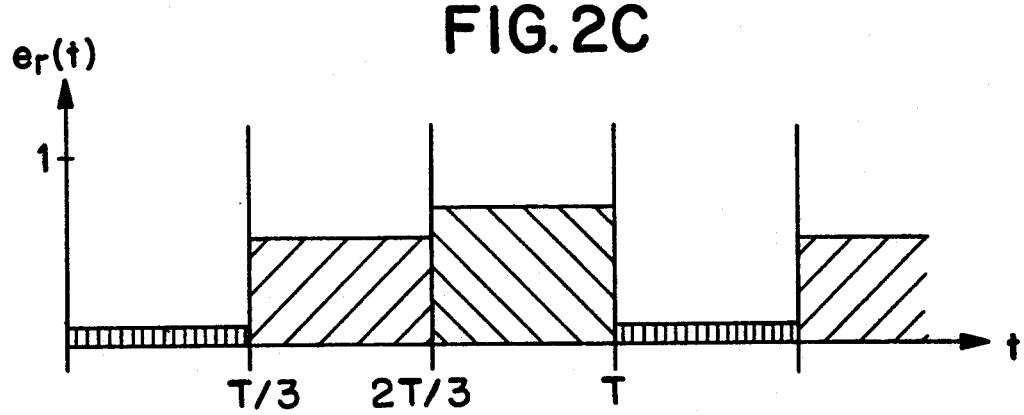
Figure 3:
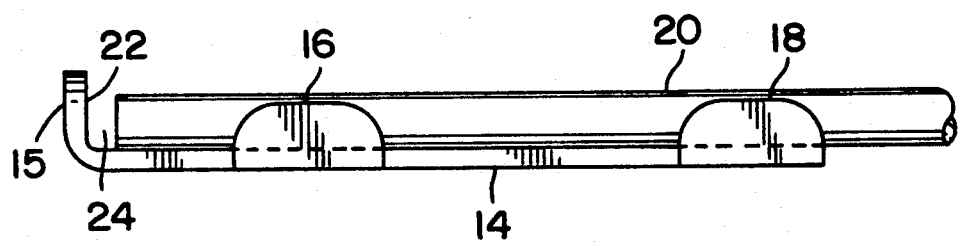
FIG. 3 is a side view of the reflector assembly portion of an apparatus, according to the instant invention.
Figure 4:
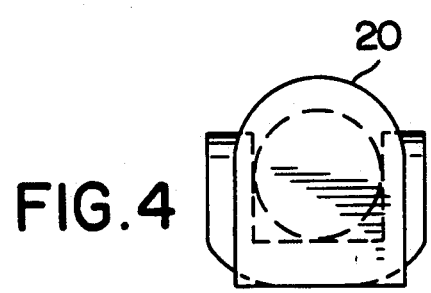
FIG. 4 is an end view of the reflector assembly of FIG. 3.
Figure 5:
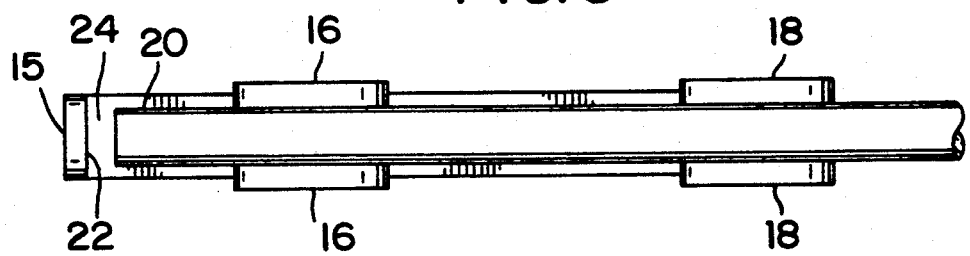
FIG. 5 is a top view of the reflector assembly of FIG. 3.

FIGS. 2A, 2B and 2C show reflectance signals for (1) a "white" target, where the ratio of "green" to "red" light is 1; (2) a "red" target, where the ratio of "green" to "red" light is 0.72; and (3) a "green" target, where the ratio of "green" to "red" light is 1.15. The difference in the signals provided during one cycle (dark to red to green) is shown. By exposing the reflector to different wavelengths of light, and determining the ratios of reflected light, it is possible to determine a change in a physical property, such as color, of the reflected light. The difference in the reflectance signals of FIGS. 2A, 2B and 2C therefore shows the sensitivity of the present invention.

It is to be understood that ideally, the present invention does not require initialization or constant standardization against a reference value in order to achieve the purpose of detecting failure of the membrane. However, because various elements in the system could be affected by such influences as temperature or humidity, it is preferred that initialization and standardization procedures be employed. Accordingly, it will be understood that as technological improvements resolve the factors influencing radiation reflection, then the procedures of initialization and standardization may become less important and eventually, may be omitted without departing from the inventive concept herein described.

In the present invention, a single light wavelength or a single white light of multiple wavelengths may be employed. However, the procedures of initialization and standardization are better served by the use of light with different specific wavelengths. Further, by selecting specific wavelengths of light it is possible to render the system of the invention color specific. For example, such color specificity would have particular use in catheter systems that typically permit migration of water or water vapor through the balloon membrane while the catheter system is in use. Since water and water vapor is essentially colorless, it will not cause a color-specific system to trigger an alarm. In this way, false alarms can be easily avoided.

Light that is transmitted by optical fiber 20 traverses through the fluid present in gap 24, is partially absorbed, and is reflected back into fiber 20. By determining the ratio of reflected light at the two different wavelengths, as described above, it is possible to detect the presence of a contaminant.

The optical fiber of the FIG. 7 embodiment is shown as comprising two fibers: input fiber 20a and reflected output fiber 20b. As indicated by the arrows, input fiber 20a transmits light to illuminate reflector 28 and output fiber 20b transmits the reflected light from the absorbent medium of reflector 28. As those in the art will readily understand, by using directional couplers that are well known in the art, it is possible to replace fibers 20a and 20b with a single fiber.

Although the above embodiments detect the presence of contaminants such as blood by detecting color change using visible light, other detectable properties may be used. Further, radiation above or below the visible range may be used, as appropriate.

While the method and system of this invention have been described above in connection with several specific embodiments, it should be understood that numerous modifications could be made by persons of skill in this art without departing from the scope of this invention. Accordingly, the above description is intended to be merely illustrative and not limiting. The scope of the invention claimed should be understood as including all those alternatives and modifications that the above description would readily suggest or that would readily occur or be apparent to one skilled in the art upon reading the above.

What is claimed is:

1. A method for detecting a contaminant in a balloon catheter comprising the steps of:
    a) transmitting light radiation to a region within said balloon catheter where the presence of a contaminant is to be detected;
    b) reflecting said radiation to sensor means;
    c) permitting the presence of said contaminant to change a physical characteristic of said reflected radiation; and,
    d) detecting said change in said physical characteristic.

2. The method of claim 1 wherein the light radiation has at least two separate and distinct wavelengths.

3. A method for detecting a contaminant in a catheter having a distal end and a proximal end comprising the steps of:
    a) disposing a reflector in a distal end of the catheter;
    b) irradiation the reflector with light radiation;

c) detecting radiation reflected by the reflector;
d) permitting the contaminant to change a physical property of the reflected radiation; and,
e) detecting the change in said physical property.

4. A method for detecting a contaminant in a catheter having a distal end and a proximal end comprising the steps of:
   a) disposing a reflector in a distal end of the catheter;
   b) irradiating the reflector with electromagnetic radiation, including the steps of disposing an optical fiber between the distal end and the proximal end of said catheter, and transmitting said radiation through said fiber from said proximal end to said distal end;
   c) detecting radiation reflected by the reflector;
   d) permitting the contaminant to change a physical property of the reflected radiation; and
   e) detecting the change in said physical property.

5. A method for detecting a contaminant in a balloon catheter positioned within a fluid passageway of a patient's body comprising the steps of:
   a) placing a balloon catheter within said passageway, said balloon catheter having a catheter portion and a balloon portion, a reflector within either said balloon portion or said catheter portion, and means for irradiating said reflector with light radiation and for transmitting light radiation reflected from said reflector;
   b) irradiating said reflector with light radiation;
   c) reflecting said radiation to a detector; and,
   d) determining a change in a physical property of said reflected radiation when a contaminant is present.

6. The method of claim 5, wherein said irradiating step includes irradiating said reflector with at least two beams of light radiation having at least two different wavelengths.

7. The method of claim 5, wherein said irradiating step includes irradiating said reflector with at least first and second light wavelengths.

8. The method of claim 7, further including the steps of measuring the intensity of reflected light for each of said first and second light wavelengths, and comparing said intensities of reflected light wavelengths.

9. The method of claim 8, further including the step of adjusting the intensity of said first and second light wavelengths to have equal signal strength.

10. The method of claim 9, further including the steps of:
    a) determining a reference signal strength where no radiation is provided (Rdi), a reference signal strength for said first light wavelength (Rgi), and a reference signal strength for said second light wavelength (Rri);
    b) determining a reference ratio constant Kr according to the formula:

$$Kr = (Rgi - Rdi)/(Rri - Rdi); \text{ and,}$$

c) varying the light intensity of at least said first light wavelength to maintain Kr at a constant value.

11. The method of claim 8, wherein said comparing step includes determining the ratio:

$$C = (Sg - Sd)/(Sr - Sd)$$

where Sg is a signal indicating the light intensity of said first light wavelength, Sd is a signal in the absence of radiation, and Sr is a signal indicating the light intensity of said second light wavelength, wherein a value of C different from about 1 indicates the presence of a contaminant.

12. The method of claim 7, wherein said first light wavelength is green and said second light wavelength is red.

13. The method of claim 5, wherein said irradiating step includes sequentially illuminating said reflector with first and second light wavelengths.

14. A method for detecting blood in a balloon catheter positioned within a fluid passageway of a patient's body comprising the steps of:
    a) placing a balloon catheter within said passageway, said balloon catheter having a catheter portion and a balloon portion, a reflector within either said balloon portion or said catheter portion, means for illuminating said reflector with light, and means for detecting light reflected by said reflector;
    b) illuminating said reflector with at least first and second light wavelengths;
    c) detecting the light reflected from said reflector for each of said first and second light wavelengths;
    d) measuring the intensity of said reflected light at each of said first and second light wavelengths; and,
    e) comparing said intensities of reflected light for said first and second light wavelengths.

15. A system for detecting a contaminant in a balloon catheter having proximal and distal ends comprising:
    a) means for transmitting light radiation to a region within said catheter where the presence of a contaminant is to be detected;
    b) means for reflecting said radiation to sensor means; and,
    c) sensor means for detecting changes in a physical property of said reflected radiation.

16. The system of claim 15, wherein said means for transmitting light radiation comprises:
    a) an optical fiber disposed between the distal end and a proximal end of said catheter; and,
    b) means for alternately irradiating said proximal end of said optical fiber with at least two wavelengths of light.

17. A system for detecting a contaminant in a balloon catheter positioned within a fluid passageway of a patient's body, comprising:
    a) a balloon catheter having a catheter portion and a balloon portion wherein said catheter portion has a proximal and a distal end and wherein said balloon portion is at or near said distal end;
    b) a reflector disposed within either said balloon portion or said catheter portion;
    c) means disposed in said catheter portion for transmitting light radiation between said proximal and distal ends; and,
    d) means for detecting the radiation reflected by said reflector.

18. The system of claim 17, further including means for generating light beams of at least a first wavelength and a second wavelength, and wherein said system further includes means for measuring the intensity of reflected light for said first and/or second light wavelengths.

19. The system of claim 18, further comprising means for comparing the intensities of reflected light for said first and said second wavelengths.

20. The system of claim 19, wherein said means for comparing includes means for determining the ratio:

$$C = (Sg - Sd)/(Sr - Sd)$$

where Sg is a signal indicating the light intensity of said first light wavelength, Sd is a signal in the absence of radiation, and Sr is a signal indicating the light intensity of said second light wavelength, wherein a value of C different from about 1 indicates the presence of a contaminant.

21. The method of claim 20, wherein a gap is provided between said reflector and the distal end of said radiation transmission means and wherein the value of C is about 1 when said gap is free of any contaminant.

22. The system of claim 18, further comprising means for adjusting the intensity of said first and second light wavelengths to have equal signal strength.

23. The system of claim 18, further including:
 a) means for determining a reference signal strength where no radiation is provided (Rdi), a reference signal strength for said first light wavelength (Rgi), a reference signal strength for said second light wavelength (Rri), and
 b) means for determining a reference ratio constant Kr according to the formula:

$$Kr = (Rgi - Rdi)/(Rri - Rdi); \text{ and,}$$

c) means for varying the light intensity of at least said first light wavelength to maintain Kr at a constant during radiation transmission.

24. The system of claim 18, wherein said first light wavelength is green, and said second light wavelength is red.

25. The system of claim 18, further including means for sequentially illuminating said reflector with said first and second light wavelengths.

26. The system of claim 18, wherein said system is capable of detecting deterioration of at least one of the reflector, the light transmission means, and the light generating means.

27. The system of claim 17, wherein said means for transmitting light radiation comprises optical fiber means.

28. The system of claim 27, wherein said optical fiber means is a single 250 micron optical fiber.

29. A system for detecting a contaminant in a balloon catheter positioned within a fluid passageway of a patient's body, comprising:
 a) a balloon catheter having a catheter portion and a balloon portion wherein said catheter portion has a proximal and a distal end and wherein said balloon portion is at or near said distal end;
 b) a reflector disposed within either said balloon portion or said catheter portion, wherein said reflector has a mirrored surface;
 c) means disposed in said catheter portion for transmitting electromagnetic radiation between said proximal and distal ends; and,
 d) means for detecting the radiation reflected by said reflector.

30. A system for detecting a contaminant in a balloon catheter positioned within a fluid passageway of a patient's body, comprising:
 a) a balloon catheter having a catheter portion and a balloon portion wherein said catheter portion has a proximal and a distal end and wherein said balloon portion is at or near said distal end;
 b) a reflector disposed within said balloon portion, said reflector being comprised of the inner surface of said balloon portion;
 c) means disposed in said catheter portion for transmitting electromagnetic radiation between said proximal and distal ends; and,
 d) means for detecting the radiation reflected by said reflector.

31. A system for detecting a contaminant in a balloon catheter positioned within a fluid passageway of a patient's body, comprising:
 a) a balloon catheter having a catheter portion and a balloon portion wherein said catheter portion has a proximal and a distal end and wherein said balloon portion is at or near said distal end;
 b) a reflector disposed within either said balloon portion or said catheter portion, wherein said reflector is comprised of absorbent material the reflectivity of which changes in the presence of a contaminant;
 c) means disposed in said catheter portion for transmitting electromagnetic radiation between said proximal and distal ends; and,
 d) means for detecting the radiation reflected by said reflector.

32. The system of claim 31 wherein said reflector substantially touches the radiation transmission means.

33. The system of claim 31 wherein the reflector is normally white but changes color upon contact with a contaminant.

34. The system of claim 31 wherein the absorbent material is selected so that its reflectivity at a given wavelength changes in the presence of at least one contaminant but does not change in the presence of at least one different contaminant.

35. A system for detecting a contaminant in a balloon catheter positioned within a fluid passageway of a patient's body, comprising:
 a) a balloon catheter having a catheter portion and a balloon portion wherein said catheter portion has a proximal and a distal end and wherein said balloon portion is at or near said distal end;
 b) a reflector disposed within either said balloon portion or said catheter portion;
 c) means disposed in said catheter portion for transmitting electromagnetic radiation between said proximal and distal ends; and,
 d) means for detecting the radiation reflected by said reflector;
 wherein said system is capable of detecting blood in an amount as small as 0.5 cc.

36. A system for detecting a contaminant in a balloon catheter positioned within a fluid passageway of a patient's body, comprising:
 a) a balloon catheter having a catheter portion and a balloon portion wherein said catheter portion has a proximal and a distal end and wherein said balloon portion is at or near said distal end;
 b) a reflector disposed within either said balloon portion or said catheter portion, wherein said reflector comprises an absorbent medium;
 c) means disposed in said catheter portion for transmitting electromagnetic radiation between said proximal and distal ends; and,
 d) means for detecting the radiation reflected by said reflector.

37. A system for detecting a contaminant in a balloon catheter positioned within a fluid passageway of a patient's body, comprising:

a) a balloon catheter having a catheter portion and a balloon portion wherein said catheter portion has a proximal and a distal end and wherein said balloon portion is at or near said distal end;
b) a reflector disposed within either said balloon portion or said catheter portion;
c) means disposed in said catheter portion for transmitting electromagnetic radiation between said proximal and distal ends; and,
d) means for detecting the radiation reflected by said reflector;
wherein a gap is provided between said electromagnetic radiation transmission means and said reflector.

38. A system for detecting blood in a balloon catheter positioned within a fluid passageway of a patient's body comprising:
a) a balloon catheter having a catheter portion, a balloon portion, a proximal end and a distal end, with said balloon portion being disposed at or near said distal end;
b) a reflector disposed within either said balloon portion or said catheter portion;
c) optical means located in said catheter portion for sequentially illuminating said reflector with at least first and second light wavelengths, and for detecting the reflected light reflected from said reflector for said first and second wavelengths;
d) means for measuring intensities of said reflected light; and,
e) means for comparing said intensities of reflected light.

39. An intra-aortic balloon catheter comprising:
a) a catheter tube having a proximal end and a distal end;
b) a balloon membrane at or near the distal end of said catheter tube, said membrane being inflatable to form a balloon chamber;
c) means for transmitting light radiation at least to the vicinity of the distal end of said catheter tube; and
d) means for reflecting said light radiation.

40. The intra-aortic balloon catheter of claim 39 wherein said electromagnetic transmission means comprises optical fiber means.

41. The intra-aortic balloon catheter of claim 40 wherein said optical fiber means are disposed within the interior of the catheter tube.

42. The intra-aortic balloon catheter of claim 41 wherein said reflecting means and said optical fiber means are positioned such that at least some of the radiation reflected from said reflecting means enters said optical fiber means.

43. A method for detecting a contaminant in a catheter having a distal end and a proximal end comprising the steps of:
a) disposing a reflector in a distal end of the catheter;
b) irradiating the reflector with light radiation, wherein the light radiation has at least two separate and distinct wavelengths;
c) detecting radiation reflected by the reflector;
d) permitting the contaminant to change a physical property of the reflected radiation; and
e) detecting the change in said physical property.

* * * * *

UNITED STATES PATENT AND TRADEMARK OFFICE
CERTIFICATE OF CORRECTION

PATENT NO. : 5,201,755
DATED : April 13, 1993
INVENTOR(S) : Klement

It is certified that error appears in the above-identified patent and that said Letters Patent is hereby corrected as shown below:

COLUMN 5:

Line 41, "radioopaque" should read --radiopaque--.

COLUMN 6:

Line 40, "Coupler" should read --coupler--.

COLUMN 8:

Line 68, "irradiation" should read --irradiating--.

COLUMN 11:

Line 26, "Kr = (Rgi = Rdi) / (Rri = Rdi); and," should
  read --Kr = (Rgi - Rdi) / (Rri - Rdi); and,--.

COLUMN 14:

Line 11, "electromagnetic" should read --light--.

Signed and Sealed this

Fourteenth Day of December, 1993

Attest:

BRUCE LEHMAN

*Attesting Officer*   *Commissioner of Patents and Trademarks*